United States Patent [19]

Moore

[11] Patent Number: Plant 7,128

[45] Date of Patent: Jan. 30, 1990

[54] MINIATURE ROSE PLANT NAMED 'MORCARLET'

[75] Inventor: Ralph S. Moore, Visalia, Calif.

[73] Assignee: Sequoia Nursery, Visalia, Calif.

[21] Appl. No.: 300,592

[22] Filed: Jan. 23, 1989

[51] Int. Cl.[4] ..... A01H 5/00

[52] U.S. Cl. ..... Plt./10

[58] Field of Search ..... Plt./10

*Primary Examiner*—James R. Feyrer

[57] ABSTRACT

The subject of the present disclosure is a new and distinct variety of miniature rose plant characterized by well mossed buds and deep red flowers of good substance and keeping qualities.

1 Drawing Sheet

1

The present invention relates to a new and distinct variety of hardy, dwarf, bush type rose plant of the miniature class; the variety being primarily characterized—as to novelty—by deep red buds and flowers with the buds heavily mossed. The general color effect being deep red.

The variety is further characterized by:

An abundance of bloom, with flowers, on mature plant, borne both singly and several together in loose spray or cluster.

Little or no fragrance.

A plant which is vigorous, of bushy, somewhat upright shape with semi-glossy to glossy, small foliage with pointed leaflets; the buds and flowers being similar in form to Sheri Anne (Miniature—U.S. Plant Pat. No. 3,826).

The plant, which has a normal height of 18 to 20 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery, located at Visalia, Calif. under conditions of careful control and observation, as a cross between an un-named seedling (Dortmund×-(Dortmund×un-named striped miniature)) as the seed parent and an un-named mossed red miniature seedling as the pollen parent (the code name of this cross being Dortsing×GA822).

Subsequent to origination of the variety I successfully reproduced it, at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; upright; seedling; greenhouse; outdoors; cut flowers; garden decoration.

Class: Miniature.

*International identification.*—variety: Morcarlet.

*Commercial synonym.*—Scarlet Moss.

2

Flowers borne: Often singly but also in loose sprays of 3 to 5 or more on slender wirey stems.

Quantity of bloom: Abundant both outside and in greenhouse.

Bud:

*Peduncle.*—Rather long; slender but sturdy; erect; medium green, sometimes lightly tinted bronze (outdoors).

*Hairs.*—Numerous fine shoft hairs or "moss". Before calyx breaks; size — small. Form: long; pointed with many moss-like appendages (modified prickles) and numerous very small hairs on surface of bud; with foliaceous parts extending beyond the tip of the bud equal to one-half or less of its length.

*Color.*—Medium green, occasionally tinted with bronze (outdoors). As calyx breaks, color — dark red.

*Opening.*—Opens well in all weather.

Bloom:

*Size when fully open.*—Small, averaging about 50 mm (2").

*Petalage.*—Semi-double — averaging about 12–15 petals arranged regularly plus often several small petaloids.

*Form.*—High centered then becoming more rounded to flat with petals reflexing loosely outward, and later at maturity remaining loosely outward. Open flowers show stamens.

Petals: Fairly thick; satiny to velvety on inside and satiny on outside surface.

*Shape.*—Outside petals, broad lanceolate (almost round); short acute tip; intermediate — broad lanceolate with short acute tip; inside — lanceolate with acute tip.

Color: Newly opened flower from a plant grown in plastic greenhouse (September 1988), Visalia, Calif.

*Outside petal.*—Outside surface — near Cardinal Red 822 but veined or shaded darker, especially near edge of petal. Inside surface — dark red, near Cardinal Red 822/2, sometimes blended or veined lighter or darker.

*Intermediate petal.*—Outside surface similar to outside petal. Inside surface similar to outside petal.

*Inner petal.*—Outside surface — similar to intermediate petal. Inside surface — similar to intermediate petal. General color effect; newly opened flowers — deep red. Three days open — color similar. Behavior — opens well in all weather. Spent petals drop off. Flower longevity (May 1988) — plant in pot 5–7 days or longer. Cut flowers at living room temperature 4–6 days or longer.

Reproductive organs:

*Stamens.*—Several, arranged regularly about pistils.

*Filaments.*—Varying length, medium long, light yellow.

*Anthers.*—Yellow.

*Pollen.*—Fair amount.

*Pistils.*—Average number.

*Styles.*—Fairly even; medium length; bunched; color — yellowish.

*Ovaries.*—All enclosed in calyx.

*Hips.*—Some; ball shaped; orange to red; covered with stiff mossy prickles.

*Sepals.*—Permanent; spear shape; remaining (more or less) at right angle to peduncle and covered on lower (outer) side with numerous soft moss like appendages.

*Seed.*—Few to several.

Foliage:

*Leaves.*—Compound of five (sometimes three or seven) leaflets; fairly small to medium; leathery; semi-glossy to glossy.

*Leaflets.*—Shape: broad, lanceolate; apex acute; base rounded (sometimes acute). Margin serrate. Color: medium to dark green; new growth — normal (medium) green — sometimes reddish (outdoors). Rachis: medium strength; upperside may have numerous very tiny short hairs, grooved; underside several hooked thorns with numerous tiny prickles. Stipules: short to medium length; narrow to medium width; short length; narrow points which turn out usually at about 45 degrees (sometimes more or less).

Growth:

*Habit.*—Dwarf; bushy; rounded to upright; much branched.

*Growth.*—Free vigorous; internodes fairly short.

*Canes.*—Medium slender; sturdy.

*Main stems.*—Color: medium green.

*Thorns.*—Numerous; slender; straight. Prickles — some.

*Branches.*—Color: medium green. Thorns: numerous. Prickles: some. Hairs: fairly numerous.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded to upright, much branched habit, substantially as illustrated and described, characterized by buds and flowers of a dark red color which may be modified by darker shading or veining; the bud and flower resembling the variety Sheri Anne (U.S. Plant Pat. No. 3,826) in form, the sepals of each bud being covered with numerous moss like appendages; and further characterized by a plant of vigorous and compact growth habit, easy to propagate from cuttings or by budding, with an abundance of small to medium size semi-glossy to glossy foliage and an abundance of flowers borne singly and in loose clusters of 3 to 5 or more.

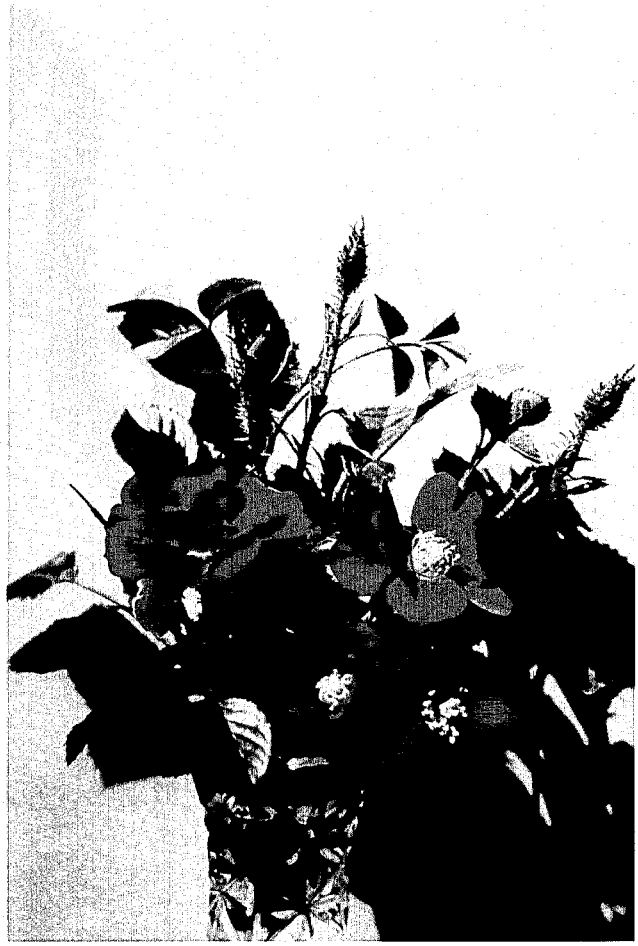

* * * * *